United States Patent [19]

Takata

[11] Patent Number: 4,787,390
[45] Date of Patent: Nov. 29, 1988

[54] ELECTRODE SENSOR
[75] Inventor: Akihiko Takata, Tokyo, Japan
[73] Assignee: Scovill Japan Kabushiki Kaisha, Tokyo, Japan
[21] Appl. No.: 41,437
[22] Filed: Apr. 23, 1987
[51] Int. Cl.[4] .............................................. A61B 5/04
[52] U.S. Cl. ...................................... 128/641; 128/802
[58] Field of Search ................................ 128/639–641, 128/803, 798, 802, 644

[56] References Cited

U.S. PATENT DOCUMENTS

| | | | |
|---|---|---|---|
| 3,820,531 | 6/1974 | Szpur | 128/641 |
| 3,841,312 | 10/1974 | Corasanti | 128/641 |
| 3,923,042 | 12/1975 | Hajdu et al. | 128/641 |
| 4,161,174 | 7/1979 | Mercuri | 128/641 |
| 4,196,737 | 4/1980 | Bevilacqua | 128/798 |
| 4,441,501 | 4/1984 | Parent | 128/641 |
| 4,635,641 | 1/1987 | Hoffman | 128/639 |

FOREIGN PATENT DOCUMENTS 8605083  9/1986  Fed. Rep. of Germany ...... 128/641

*Primary Examiner*—Max Hindenburg
*Assistant Examiner*—Angela D. Sykes
*Attorney, Agent, or Firm*—Marshall, O'Toole, Gerstein, Murray & Bicknell

[57] ABSTRACT

An electrode sensor for a biomedical electrode of the button type comprises a plastic base which consists of a shank to be clinched to fill up the cavity of an expanded hollow head of an electrode button and a base flange formed in one piece of the shank, and an electrically conductive film formed over the plastic base. The flange is bowl-shaped with a gradual upward inclination from the center toward the periphery. The flange has a plurality of projections or grooves formed on at least either its upper or under side.

2 Claims, 3 Drawing Sheets

ELECTRODE SENSOR

BACKGROUND OF THE INVENTION

This invention relates to a biomedical electrode for the measurement of bioelectric potentials.

In order to record and interpret electrocardiographic, encephalographic, and other bioelectric phenomena, it is essential to use appropriate biomedical electrodes. In recent years, the requirements in clinical rehabilitation and for physiological studies have increasingly called for uninterrupted electrocardiographic and other recordings of the subjects without restraint upon their freedom in daily life. For these purposes there is an eager demand for highly efficient and yet lightweight and inexpensive biomedical electrodes.

Among the existing biomedical electrodes, relatively excellent in performance are those of the button type. (Refer, e.g., to Japanese Patent Application Publication No. 46849/1981.) In FIG. 1, a commercially available biomedical electrode of the button type is digrammatically shown as comprising a metallic electrode button 1, an electrode sensor 2, an artificial skin adapter 3 (a fabric, paper, or plastic sheet) held between the button and sensor, and an artificial skin 4 (a sponge sheet or the like impregnated with an electrolyte or in a gelled state or the like) secured to the electrode sensor and adapter on one side and adapted to fit the human skin on the other side. Terminals of a measuring circuit not shown are connected to the button 1 by sockets, clips or the like not shown. The sensor 2 consists of a plastic base and an electrically conductive film of silver=silver chloride composite material or the like covering the base surface. The plastic base is employed for the sensor 2 to resist the corrosive attack of the electrolyte and also to replace the expensive metals usually used to make the sensors.

A drawback of the plastic-based sensor is that its flange is not strong enough to hold the adapter 3 firmly in place. If adequate strength is to be attained, the flange must have increased wall thickness. A thicker flange, however, would objectionably protrude if the adapter were thin, causing the artificial skin to bulge accordingly and rendering it infeasible to make intimate contact with the electrode sensor and the human skin, as indicated in FIG. 2. An attempt to remove this drawback might be to use a thicker adapter 3 and embed the flange partly in it as well as in the artificial skin. However, the arrangement would mar the total flexibility of the artificial skin and again make its intimate contact with and adhesion to the human skin impossible. In view of these, there is a strong demand for a biomedical electrode in which both the flange of the sensor 2 and the adapter 3 are as thin as possible while the flange retains adequate strength.

This invention aims at providing an electrode sensor which takes a firm hold of the adapter and comes in intimate contact with and attains good adhesion to the skin.

SUMMARY OF THE INVENTION

The present invention provides an electrode sensor of an improved structure for use in a biomedical electrode which comprises, in addition to the sensor, an electrode button engaged with the sensor, an artificial skin adapter secured between the above two members, and an artificial skin.

The electrode sensor according to the invention comprises a plastic base having a shank the upper portion of which can be clinched with respect to an electrode button and a base flange formed in one piece with the shank, and an electrically conductive film formed over the plastic base, the flange being bowl-shaped with a gradual upward inclination from the center toward the periphery. In a preferred embodiment the thickness of the flange is gradually decreased from the center toward the periphery. In further preferred embodiments the upper side of the flange is formed with a plurality of small projections for added strength of the hold of the flange on the adapter.

When the electrode sensor of the invention is assembled with an electrode button holding an artificial skin adapter in between, the gradually upwardly inclined periphery of the flange of the electrode sensor is flattened against the inherent elasticity of the flange, thus enhancing the hold of the flange on the adapter. This, in turn, makes possible the use of a thinner flange and a corresponding decrease in the adapter thickness. In this way the adapter can be firmly held in place and the biomedical electrode can attain an intimate contact with and good adhesion to the human skin. The thinner periphery of the flange than heretofore smoothens and further improves the adhesion of the side of the flange that faces the artificial skin. The small projections on the upper side of the flange ensures a firmer hold of the flange on the adapter.

DESCRIPTION OF THE PREFERRED EMBODIMENT

Figure 1:
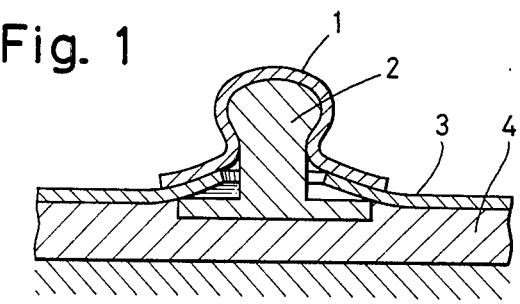
FIG. 1 is a sectional view of a conventional biomedical electrode.
Figure 2:
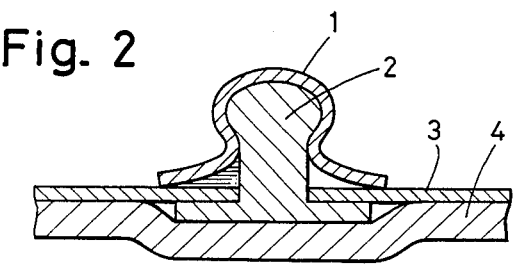
FIG. 2 is a sectional view of a biomedical electrode having an ordinary plastic-base electrode sensor.
Figure 3:
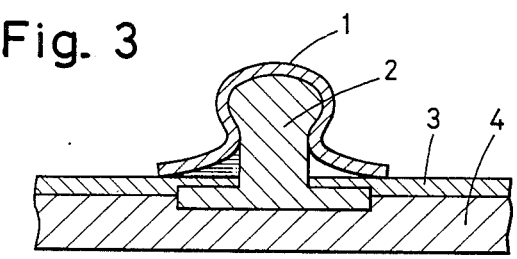
FIG. 3 is a sectional view of a similar biomedical electrode of the prior art.

The present invention will be more fully described below with reference to the accompanying drawings. While a biomedical electrode using the electrode sensor of the invention is described herein as having a structure corresponding to that of the conventional biomedical electrode illustrated in FIGS. 1 to 3, the electrode can be variously modified provided it incorporates the electrode sensor of the invention.

Figure 4:
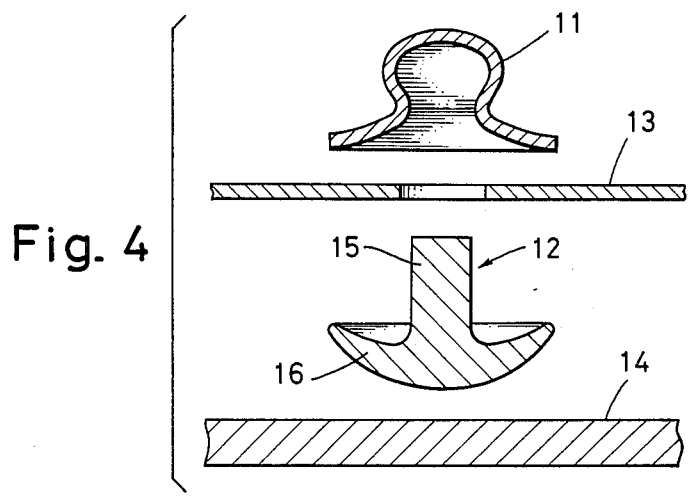
FIG. 4 is an exploded sectional view of a biomedical electrode including an electrode sensor according to the invention.
Figure 5:
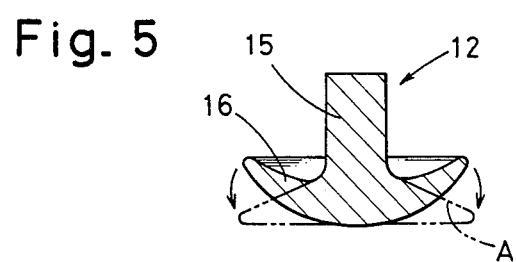
FIG. 5 is an enlarged view of the electrode sensor.

The biomedical electrode is shown as exploded in FIG. 4 and as assembled in FIG. 5. It comprises an electrode button 11, an electrode sensor 12 according to this invention, an adapter 13, and an artificial skin or pad 14. Excepting the electrode sensor, the components may be conventional ones. For example, stainless steel, nickel-plated brass, nickel-silver-plated brass or the like is used for the button 11. The adapter 13 is a sheet of fabric, paper, plastic or the equivalent. It may be made electrically conductive by the incorporation of a conductive fiber or like substance. The artificial skin 14 consists of a sheet of sponge impregnated with a paste containing an electrolyte such as common salt. Instead, the sponge may be gelled or made self-adhesive, or even an adhesive layer may be applied to its surface. It is further possible to omit the artificial skin 14 and apply a conductive paste to the entire back sides of the electrode sensor and adapter.

The electrode sensor is made of a tough, strong plastic molding capable of being clinched, coated with an electrically conductive substance. It has a shank 15 and a base flange 16 formed in one piece. The conductive coat on its surface is formed of silver or silver-silver chloride by plating or with the application of pressure. The silver-silver chloride coating material offers advantages including low bioelectrical potential, stability against temperature, no change in bioelectric potential with time, no noise generation as a source, and limited impedance.

The basic structure of the electrode sensor 12 is illustrated in FIG. 5. From FIG. 5 onward it will be taken for granted that the electrode sensor is conductively coated and no reference will be made to it except when it becomes necessary. The base flange 16 that combines with the clinchable shank 15 to constitute the electrode sensor looks like an inverted mushroom, with the wall thickness gradually decreased from the center toward the peripheral edge while inclining upwardly. The degree of inclination and the change in wall thickness are chosen so that, when the shank 15 has been clinched to assemble the biomedical electrode, the flange 16 is forced down as indicated by the arrows in FIG. 5, with sufficient elastic force to exert an adequate pressure on the adapter 13. These factors can be easily determined experimentally.

Figure 6:
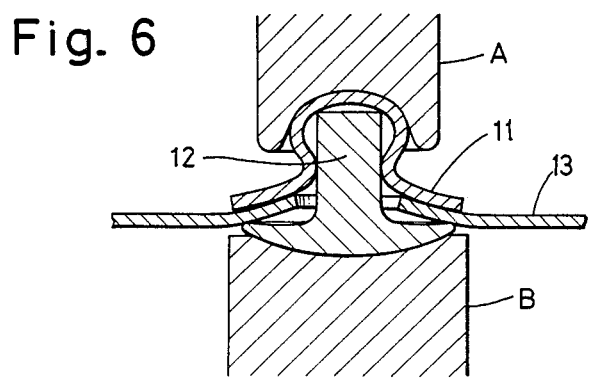
FIG. 6 is a sectional view illustrating the process of clinching during the assembling of the biomedical electrode shown in FIG. 4.
Figure 7:
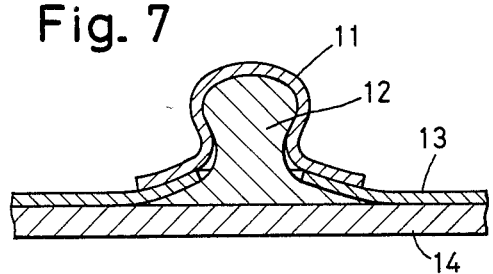
FIG. 7 is a sectional view of the biomedical electrode completed by the clinching illustrated in FIG. 6.

The shank 15 of the electrode sensor is inserted through a center hole of the adapter 13 into the cavity of the expanded hollow head of the electrode button 11. It is then clinched in place by a combination of upper and lower die members A, B. The upper portion of the shank is thus deformed to fill up the cavity of the electrode button 11, joining the button 11 and the sensor 12 permanently. During the course of clinching, the flange 16 is depressed by the button 11 and deformed downwardly as indicated by the arrows in FIG. 5 into the shape shown in FIG. 6. The flange 16 thus presses the current distributor or adapter 13 against the periphery or skirt of the electrode button 11, keeping them in relative position. As shown in FIG. 7, the artificial skin 14 is affixed to the underside of the sensor 12 and to that of the adapter 13 to complete the assembling of the biomedical electrode.

MODIFICATION EXAMPLE 1

Figure 8B:
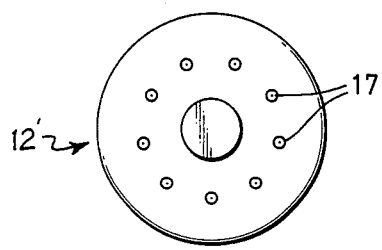
FIG. 8 shows a modification of the electrode sensor, (A) being a sectional view and (B) a plan view.
Figure 8A:
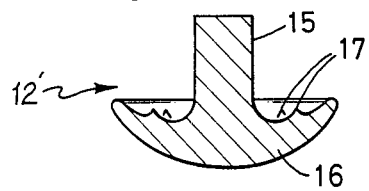

In FIG. 8, a modified electrode sensor 12' is shown. With the exception that it has a plurality of small projections 17 on the upper surface of the flange, this electrode sensor is the same as the embodiment shown in FIGS. 5 to 7. The small projections bite into the adapter, enabling the sensor to take a firmer hold of it.

MODIFICATION EXAMPLE 2

Figure 9B:
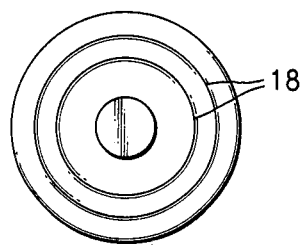
FIG. 9 shows another modification of the electrode sensor, (A) being a sectional view and (B) a plan view.
Figure 9A:
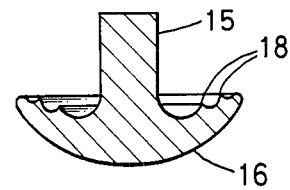

In another modification shown in FIG. 9, concentric circular projections 18 are formed on the upper surface of the flange. This arrangement also strengthens the grip of the sensor on the adapter.

OTHER MODIFICATIONS

Figure 10:
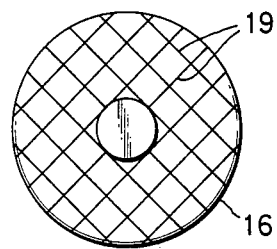
FIGS. 10 to 12 are plan views of three other modifications in which the underside of the flange of the electrode sensor is respectively modified.
Figure 11:
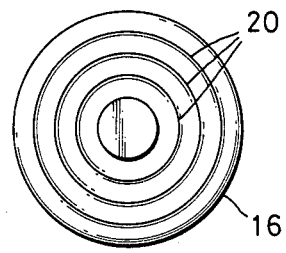
Figure 12:
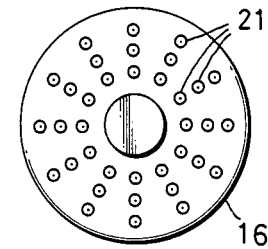

The other modifications shown in FIGS. 10 to 12 have grooves or projections formed on the underside of the flange 16 for an added surface area and therefore increased area of contact with the artificial skin 14. FIG. 10 shows a lattice of grooves 19, FIG. 11 a plurality of concentric circular projections 20, and FIG. 12 a number of small projections.

As described above, the flange of the electrode sensor according to the invention is bowl-shaped with an upward inclination from the center to the periphery. Clinching the shank of the electrode sensor with respect to the electrode button, therefore, elastically deforms the flange with the consequence that the flange securely presses the adapter against the electrode button. A flange, reduced in thickness, can well retain in place the adapter that serves as a current distributor. The thinned flange will not produce steps between the back side of the electrode sensor and the current distributor, and all will attain good contact with the artificial skin or the human skin, allowing the biomedical electrode to be infallibly attached to the human body surface.

What is claimed is:

1. An electrode sensor for use with an electrode button having an expanded hollow head forming a cavity, said sensor comprising a plastic base including a shank adapted to be clinched to fill up said cavity of said expanded hollow head of said electrode button, said base further including a base flange formed integrally with said shank, and an electrically conductive firm formed over said plastic base, said base flange having a generally smoothly recessed upper side and a bowl-shaped lower side, said lower side having a gradual upward inclination from the center thereof toward the periphery thereof, and the thickness of said base flange decreasing gradually from said center toward said periphery, said base flange having a plurality of projections formed on at least one of said upper and lower sides thereof.

2. An electrode sensor for use with an electrode button having an expanded hollow head forming a cavity, said sensor comprising a plastic base including a shank adapted to be clinched to fill up said cavity of said expanded hollow head of said electrode button, said base further including a base flange formed integrally with said shank, and an electrically conductive film formed over said plastic base, said base flange having a generally smoothly recessed upper side and a bowl-shaped lower side, said lower side having a gradual upward inclination from the center thereof toward the periphery thereof, and the thickness of said base flange decreasing gradually from said center toward said periphery, said base flange having a plurality of grooves formed on at least one of said upper and lower sides thereof.

* * * * *